United States Patent [19]

Spielvogel et al.

[11] Patent Number: 5,545,397
[45] Date of Patent: Aug. 13, 1996

[54] CONTRAST AGENTS AND COMPOSITIONS FOR RADIOLOGICAL IMAGING, AND RADIOLOGICAL IMAGING METHOD UTILIZING SAME

[75] Inventors: Bernard F. Spielvogel, Cary, N.C.; Dominique Meyer, Saint-Maur-des-Fosses, France

[73] Assignees: Boron Biologicals, Inc., Raleigh, N.C.; Guerbet S.A., Cedex, France

[21] Appl. No.: 341,767

[22] Filed: Nov. 18, 1994

Related U.S. Application Data

[60] Division of Ser. No. 55,715, Apr. 28, 1993, abandoned, which is a continuation-in-part of Ser. No. 965,216, Oct. 23, 1992, abandoned, which is a continuation-in-part of Ser. No. 781,812, Oct. 23, 1991, Pat. No. 5,256,394.

[51] Int. Cl.$^6$ ........................................ A61K 33/18
[52] U.S. Cl. ........................................ 424/9.4
[58] Field of Search ................ 424/5, 9.4; 423/287, 423/292, 294

[56] References Cited

U.S. PATENT DOCUMENTS

| | | | |
|---|---|---|---|
| 3,045,049 | 7/1962 | Clark | 568/5 |
| 3,287,416 | 11/1966 | Bobinski | 568/5 |
| 3,314,990 | 4/1967 | Miller et al. | 564/9 |
| 3,334,136 | 8/1967 | Knoth, Jr. et al. | 562/556 |
| 3,376,347 | 4/1968 | Fein et al. | 568/5 |
| 3,395,182 | 7/1968 | Schroeder | 568/5 |
| 3,427,136 | 2/1969 | Knoth, Jr. | 423/285 |
| 3,551,120 | 12/1970 | Miller et al. | 423/276 |
| 4,288,585 | 9/1981 | Allcock et al. | 528/4 |
| 4,312,989 | 1/1982 | Spielvogel et al. | 546/13 |
| 4,368,194 | 1/1983 | Spielvogel et al. | 514/64 |
| 4,412,053 | 10/1983 | Neilson et al. | 528/30 |
| 4,444,972 | 4/1985 | Allcock et al. | 528/6 |
| 4,523,009 | 6/1985 | Neilson et al. | 528/399 |
| 4,705,849 | 11/1987 | Nunn et al. | 424/1.65 |
| 5,116,980 | 5/1992 | Gabel | 544/229 |
| 5,130,302 | 7/1992 | Spielvogel et al. | 514/45 |
| 5,177,198 | 1/1993 | Spielvogel et al. | 536/25.33 |

FOREIGN PATENT DOCUMENTS

| | | |
|---|---|---|
| 1229074 | 11/1966 | Germany. |
| 479772 | 4/1976 | U.S.S.R.. |
| 985706 | 3/1965 | United Kingdom. |

OTHER PUBLICATIONS

Unger et al., Anal. Chem., vol. 59(8),pp. 1145–1149 (1987).
Ishiwata, K. et al, "4–Borono– 2–(18F)flouro–DL–phenylalanine as a Target Compound for BNCT: Tumor Imaging Potential with Positron Emission Tomography," Chemical Abstracts, 1992, 116 (1) 293, Abs. No. 2906n.
Ishiwata, K. et al., "Synthesis and Radiation Dosimetry of 4–Borono–2–(18F)flouro–DL–phenylalanine: a Target Compound for PET and BNCT," Chemical Abstracts, 1991, 114 (23): 412, Abs. No. 224582b.
Biodegradable Polymers are Drug Delivery Systems, Langer, R. and Chasin, M., Eds., Marcel Dekker: New York, 1990, Chapter 5, "Polyphosphazenes as New Biomedical and Bioactive Materials," Allcock, H. R., pp. 163–193.
Cohen, S. et al, "Ionically Cross–Linkable Polyphosphazene: A Novel Polymer for Microencapsulation," J. Am. Chem. Soc., 1990 112: 7832–7833.
Langer, R., "New Methods of Drug Delivery," Science, 1990, 249: 1527–1533.
Mobashar, R. M., et al, "New Routes to Mercaptoacetylpeptide Ligand Precursors Utilizing Carboxy Terminus Pentaamminecobalt (III) Protection," Inorg. Chim, Acta, 1991, 186:139–147.
Parikh, A. S., et al, "Synthesis and Biodistribution of Radioiodinated Selenonium Salts: Potential Myocardial Imaging Agents," Journal of Labeled Compounds and Radiopharmaceuticals, 1986, 23(8): 815–824.
Knoth, Jr., W. H., et al, "Diazonium and Carbonyl Derivatives of Polyhedral Boranes," J. Am. Chem. Soc., 1964, 86(1): 115–116.
Miller, N. E., et al, "Chemistry of Boranes XVI. New Heterocyclic Boron Compound," Inorganic Chemistry, 1964, 3(8): 1196–1197.
Centofanti, E. F., et al, "Flourophosphine Ligands. VII. Difluorophosphine Adducts with Tetraborane–8," Inorganic Chem., 1969, 8(10): 2072–2074.
Wiersema, R. J. et al, "Electrochemical Preparation and Halogenation of 1,1'–u–Hydro–bis(undecahydro–closo–dodecaborate(3–), $B_{24}H_{23}3$–," Inorganic Chem., 1969, 8(10): 2074–70.
Knoth, Jr., W. H., et al, "Chemistry of Boranes IX. Halogenation of $B_{10}H_{10}$ and $B_{12}H_{12}$," Inorganic Chem., 1964, 3(2): 159–157.

*Primary Examiner*—Brian M. Burn
*Attorney, Agent, or Firm*—Steven J. Hultquist

[57] ABSTRACT

Contrast agent for X-ray imaging, consisting of a halogenated, especially iodinated or brominated, derivative of boron, having characteristics necessary for its use in X-ray imaging. The contrast agent may be used for imaging a corporeal situs by radiological techniques, comprising delivery to the corporeal situs of an imagingly effectively amount of a physiologically acceptable composition comprising the boron reagent. A variety of illustrative boron reagents is described, including vectorised boron derivatives, e.g., boron derivatives encapsulated within liposomes, fixed on or bonded to macromolecules or polymers, etc. The contrast agents, formulations, and method of the present invention may be employed for a wide variety of radiological imaging applications, e.g., excretory urography, angiocardiography, aortography, etc.

3 Claims, No Drawings

CONTRAST AGENTS AND COMPOSITIONS FOR RADIOLOGICAL IMAGING, AND RADIOLOGICAL IMAGING METHOD UTILIZING SAME

This is a division of application Ser. No. 08/055,715 filed Apr. 28, 1993 (now abandoned), which in turn is a continuation-in-part of application Ser. No. 07/965,216 filed Oct. 23, 1992 (now abandoned), which in turn is a continuation-in-part of application Ser. No. 07/781,812, filed Oct. 23, 1991 (U.S. Pat. No. 5,256,394).

BACKGROUND OF THE INVENTION

1. Field of The Invention

This invention variously relates to contrast agents for X-ray imaging, a method of imaging a visualizable corporeal situs by radiological imaging techniques (comprising delivery to the situs of an imagingly effective amount of an imagingly effective, physiologically acceptable contrast agent), and contrast media formulations useful for such imaging.

2. Description of the Related Art

In fields such as angiography, urography, and gynecology, as well as in other medical diagnostic and treatment fields, radiological imaging reagents are employed. These reagents comprise contrast agents which typically are administered in compositions or formulations to the patient or subject, for delivery to the corporeal situs part of the body) to be visualized. After administration to the body, the corporeal region to be visualized is subjected to radiation (e.g., X-ray) exposure and fluoroscopic analysis.

By way of example, radiological reagents (sometimes hereinafter referred to as "contrast agents", "contrast media", "contrast media reagents", or "imaging reagents") are delivered to a coronary situs in coronary angioplasty by means of an angiographic syringe or injector, which directs the contrast media through a catheter or other passage means into the appropriate coronary lumen. Stenosis due to vascular plaques are similarly visualized by catheter-mediated introduction of contrast medium to the vascular lumen, in connection with potential use of arterial angioplasty techniques (e.g., balloon angioplasty or laser angioplasty), by means of which the vascular plaque is treated to deocclude the arterial lumen. In gynecological diagnosis, an imaging reagent may be transcervically introduced by a syringe, pump, or injector, following which the pelvic region is radiologically visualized.

Contrast media reagents comprise a constituent imparting radiopacity thereto, typically an iodine-based compound which is physiologically acceptable, e.g., organically-bound iodine. Examples of commercially available iodine-based radiological imaging reagents include the iodine-based radiopaque contrast medium formulation which is commercially available under the trademark VASCORAY® from Mallinckrodt Corporation (St. Louis, Mo., USA).

X-ray contrast agents already known in the art include a number of halogenated derivatives, especially iodinated derivatives, of 5-amino-isophthalic acid, e.g., the halogenated derivatives described in French Patent No. 2 053 037.

While commercially available imaging formulations are of generally effective and useful character, they nonetheless have some limiting and sub-optimal characteristics attendant their use.

The contrast medium must be completely removed (flushed, or otherwise extracted) from the corporeal system following visualization of the desired situs.

The active ingredient of conventional iodine-based imaging formulations frequently has a relatively low concentration or "loading" of iodine associated therewith, as a result of which relatively high dosages of the contrast medium are required.

In addition, the active ingredients employed in many radiological imaging formulations frequently are poorly soluble in the carrier medium of the formulation.

Further, many of the X-ray contrast agents in commercial use have undesirable toxicity, osmolality, viscosity, and cost characteristics.

Accordingly, it would be an advance in the art to provide a superior radiological imaging reagent which (1) is physiologically acceptable, (2) is safe, highly effective, and efficient in character, e.g., at relatively low dosage, (3) comprises an active ingredient which is water soluble so that water may be employed as the solvent medium of the reagent formulation, (4) is excreted in normal functioning of the corporeal system, and (5) produces (aqueous) formulations characterized by low osmolality and low viscosity.

Relative to the contrast agents, radiological visualizing method, and contrast media formulations of the present invention, relevant art comprises the aforementioned French Patent 2 053 037 and the art which is described below.

U.S. Pat. No. 4,847,065 to A. Y. Akimova et al discloses iodine-containing radiopaque organic acids, as described at column 3, lines 15–21 of the patent.

U.S. Pat. No. 4,713,235 to R. E. Krall discloses organic iodo agents, particularly iodo carboxylic acids, as radiopaque agents in acrylate-based occlusion compositions for female sterilization. The iodine reagents are discussed at column 3, line 20 to column 4, line 22 of the patent.

As mentioned above, a diagnostic radiopaque formulation is commercially available from Mallinckrodt, Inc. (St. Louis, Mo.) under the trademark VASCORAY®. This contrast media formulation is a phosphate-buffered solution containing organically bound iodine.

Commercially available diagnostic radiopaque media are variously used in aortography, angiocardiography, and excretory urography.

SUMMARY OF THE INVENTION

In one aspect, the present invention relates to a contrast agent which is constituted by a halogenated, especially iodinated or brominated, derivative of boron, having characteristics rendering,it suitable for use in X-ray imaging.

Such contrast agent may for example comprise a halogenated derivative of boron, e.g., an organic halogenated derivative of boron, which is characterized by:

a stability in water sufficiently high to enable it to withstand sterilization conditions;

a high molar halogen concentration, especially iodine or bromine concentration, equal to at least 10%, preferably to at least 30% and, still more preferably, to at least 40%, and lower than 95%;

a low osmolality, lower than 2000 mosmol/kg $H_2O$, preferably lower than 800 mosmol/kg $H_2O$, at useful concentrations, i.e., higher than 100 g of halogen, especially of iodine or of bromine per liter; and a low toxicity corresponding to a $LD_{50}$ intravenously in mouse, higher or equal to 2 g of halogen, especially of iodine or bromine, per kg of body weight of a mouse test subject.

In still another aspect, the present invention relates to a method of radiologically visualizing a corporeal situs, comprising delivery to the situs of an imagingly effective amount of a physiologically acceptable contrast medium formulation comprising a radiopacity-imparting boron compound, followed by visualizing the corporeal situs with radiological imaging means.

As used herein, the term "physiologically acceptable" means that the contrast medium is biocompatible in character, with respect to its administration, contact, and action in the corporeal system with which the contrast medium is used. The term "imagingly effective" means efficacious for radiological imaging using a radiation source and visualizing means, e.g., X-ray source and fluoroscopic visualizing means.

As used herein, the term "boron compound" is intended to be broadly construed to encompass a wide variety of boron derivatives, and to include (i) compounds per so, (ii) ionic (anionic, cationic, zwitterionic) or non-ionic moieties, and/or (iii) coordinating complexes containing at least one boron atom as a constituent thereof.

Correspondingly, a "halogenated boron compound" is a boron compound having halogen atoms or ions in the boron compound as constituents thereof. The halogen, or halo, moiety may suitably comprise fluorine, chlorine, bromine, and/or iodine, and in a preferred aspect, the halogenated boron compound contains iodine or bromine.

Advantageous halogen-containing boron compounds potentially useful in the broad practice of the present invention include halogen-containing polyborane species, halogen-containing ionic and non-ionic moieties, and/or derivatives of such polyborane species and ionic and non-ionic moieties. Suitable halogen-containing boron compounds may be obtained from polyboranes (see Chemical Reviews 92, 2, 177–362, 1992).

In a specific aspect, the boron compounds of the invention for use as contrast agents include halogenated, especially iodinated or brominated, organic derivatives of boron, of the formula:

$(B_nC_mH_{(m+n-y)}M_x$  (I)

in which
n is an integer from 3 to 14, preferably from 9 to 12,
m is an integer from 0 to 2,
with m+n=5 to 14, preferably 9 to 12,
y is an integer from 1 to 14, preferably 1 to 12,
x is an integer from 0 to 4,
M is the mono- or multivalent cation of an organic or mineral base,
X is substituents, identical to or different from one another, selected from among:
halogen atoms (F, Cl, Br, I),
alkyl groups in $C_1$ to $C_{12}$, preferably in $C_1$ to $C_4$,
hydroxy, and linear, branched, or cyclic hydroxyalkyl and polyhydroxyalkyl in $C_1$ to $C_{10}$, preferably in $C_1$ to $C_6$,
carboxylic acid ester groups according to formulas (g), (h) and (i),
amide groups according to formulas (a), (b) and (j),
amine group according to formula (c), groups according to formulas of carboranes (d) and (e), and groups according to formula (f):

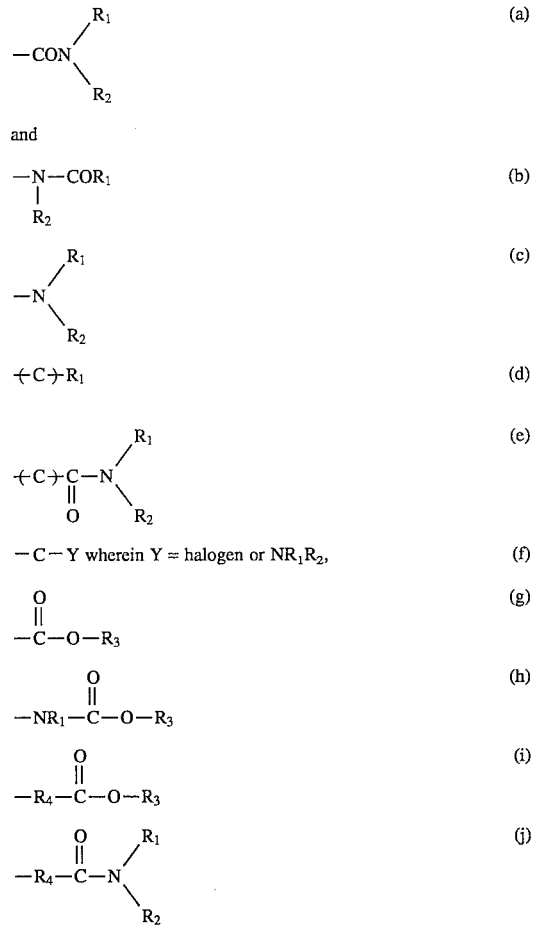

in which $R_1$ and $R_2$ are selected from hydrogen, alkyl groups in $C_1$ to $C_{12}$, preferably in $C_1$ to $C_4$, linear, branched, or cyclic hydroxyalkyl and polyhydroxyalkyl in $C_1$ to $C_{10}$, preferably in $C_1$ to $C_6$, linear or branched alkoxy groups especially in $C_1$ to $C_6$, and linear branched polyhydroxy alkoxy groups in $C_1$ to $C_{10}$;
$R_3$ represents a linear or branched alkyl group containing from one to twelve carbon atoms, a linear or branched hydroxy- or polyhydroxyalkyl group containing from one to six carbon atoms, a linear or branched alkoxyalkyl group containing from one to six carbon atoms, a linear or branched alkoxy(hydroxy) or (polyhydroxy)alkyl group containing from one to six carbon atoms; and $R_4$ represents a linear alkyl group containing from one to six carbon atoms.
the carboxylic group,
the SH group,
alkyloxy groups in $C_1$ to $C_6$,
at least one of the substituents X representing a bromine or iodine atom,
as well as the salts of the derivatives of formula (I) with one or more organic or mineral physiologically acceptable cations.

The compounds according to the invention in which at least one X group corresponds to formulas (d) and (e) are generally denoted by the term "carborane," which includes ortho, meta, and para isomers.

Alternatively, halogenated boron compounds may be employed comprising a polyphosphazene or other inorganic polymer, as a backbone structure to which halogen-containing moieties are pendently bonded or otherwise associated. Preferably, such polymeric .halogen-containing boron compounds comprise functional groups imparting water solubility to the polymer, and most preferably, the polymer comprises functionality which imparts water solubility as well as hydrolytic character, whereby the polymer may be degraded in vivo, e.g., to physiologically acceptable hydrolysis reaction products which are readily bioassimilated by and/or excreted from the corporeal system.

In another aspect, the present invention relates to various other specific novel boron compounds, as hereinafter disclosed in detail, having application in contrast media of the invention, e.g., as an active (radiopacity-imparting) ingredient in a contrast medium formulation.

In a further aspect, the novel diagnostic imaging compositions include various contrast agents in "vectorized" form, wherein the contrast agent is associated with a biocompatible "carrier" entity, which may for example comprise an encapsulant such as a liposome, or a macromolecule or polymer to which the contrast agent is fixed or bonded. Suitable vectorizing modalities are described hereinafter in specific detail.

Still other aspects of the invention include methods of making various specific imaging compounds, as hereinafter more fully described.

DETAILED DESCRIPTION OF THE INVENTION, AND PREFERRED EMBODIMENTS THEREOF

The present invention is based on the surprising and unexpected discovery that useful contrast media reagents may based on boron compounds including boron compounds known heretofore e.g., iodine-containing borohydride compounds and derivatives, as well as novel boron compounds hereinafter more fully described.

Among the boron compounds which may be usefully employed as contrast media active ingredients in the broad practice of the present invention are the boron analogs of the carbon-based reagents used in conventional X-ray imaging applications (the conventional reagents typically being benzene derivatives which are halogenated, e.g., iodinated), as well as iodinated carboranes.

A preferred class of contrast agents according to the invention consisting of halogenated, especially iodinated or brominated, organic derivatives of boron of the formula:

$$(B_nC_mH_{(m+n-y)}X_y)M_x \quad (I)$$

in which
n is an integer from 3 to 14, preferably from 9 to 12,
m is an integer from 0 to 2,
with m+n=5 to 14, preferably 9 to 12,
y is an integer from 1 to 14, preferably 1 to 12,
x is an integer from 0 to 4,
M is the mono- or multivalent cation of an organic or mineral base,
X is substituents, identical to or different from one another, selected from among:
  halogen atoms (F, Cl, Br, I),
  alkyl groups in $C_1$ to $C_{12}$, preferably in $C_1$ to $C_4$,
  hydroxy, and linear, branched, or cyclic hydroxyalkyl and polyhydroxyalkyl in $C_1$ to $C_{10}$, preferably in $C_1$ to $C_6$,
  carboxylic acid ester Groups according to formulas (g), (h) and (i),
  amide groups according to formulas (a), (b) and (j),
  amine group according to formula (c), groups according to formulas of carboranes (d) and (e), and groups according to formula (f):

 (a)

and

 (b)

 (c)

 (d)

 (e)

 (f)

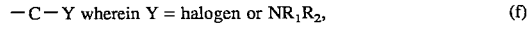 (g)

 (h)

 (i)

 (j)

in which $R_1$ and $R_2$ are selected from hydrogen, alkyl groups in $C_1$ to $C_{12}$, preferably in $C_1$ to $C_4$, linear, branched, or cyclic hydroxyalkyl and polyhydroxyalkyl in $C_1$ to $C_6$, linear or branched alkoxy groups especially in $C_1$ to $C_6$;

$R_3$ represents a linear or branched alkyl group containing from one to twelve carbon atoms, a linear or branched hydroxy- or polyhydroxyalkyl group containing from one to six carbon atoms, a linear or branched alkoxyalkyl group containing from one to six carbon atoms, a linear or branched alkoxy(hydroxy) or (polyhydroxy)alkyl group containing from one to six carbon atoms; and $R_4$ represents a linear alkyl group containing from one to six carbon atoms.

the carboxylic group,
the SH group,
alkyloxy groups in $C_1$ to $C_6$,
at least one of the substituents X representing a bromine or iodine atom, as well as the salts of the derivatives of formula (I) with one or more organic or mineral physiologically acceptable cations.

Another class of boron compounds potentially useful as contrast agents in the practice of the invention comprises halogenated (iodinated) salts of borohydrides, particularly iodinated boron salts of the formula:

wherein:
M is a monovalent or divalent cation, preferably an alkali metal or alkaline earth metal;

x is 1 when M is divalent and 2 when M is monovalent;
n is 3 to 14, preferably 10 to 12; and
y is 1 to 14, preferably 2 to 12,
and derivatives thereof, including ionic and non-ionic, and particularly anionic, species thereof.

Another class of potential contrast agents includes polyphosphazene boron compounds, including polyphosphazenes of the following formula:

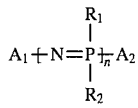

wherein:

$A_1$, and $A_2$ are end groups independently selected from hydrogen, halo, and organo which preferably are of a suitable organic constituency which is compatible with the polyphosphazene and does not preclude its efficacy for radiological imaging purposes—$A_1$ and $A_2$ may be the same or different, and may for example comprise alkyl or other hydrocarbyl radicals;

$R_1$ and $R_2$ may be the same or different, and are independently selected from hydrogen, halo, and organo groups (e.g., alkyl, haloalkyl, aryl, arylalkyl, alkenyl, alkylamino, arylamino, etc.); and n is from 2 to 20,000;

with the proviso that at least one of the $R_1$ and $R_2$ groups comprises at least one halogen atom and at least one boron atom (e.g., halogen and boron atoms may be present as $R_1$ and/or $R_2$ substituents on a single phosphorus atom of the polymer, or on more than one phosphorus atom (repeating unit) of the polymer, and which are of a suitable radiopaque character.

Cyclophosphazenes of the formula:

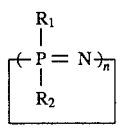

may also be advantageously employed as contrast agents in the practice of the invention,
wherein:

$R_1$ and $R_2$ are the same as above, and the compound is subject to the same proviso and radiopacity criterion as stated above, and n is from 3 to 8.

Preferably, in the cyclophosphazene and polyphosphazene boron compounds described above, at least one of the $R_1$ and $R_2$ groups comprises functionality (e.g., —NH(CH$_3$) groups) imparting water solubility to the polyphosphazene or cyclophosphazene, as the case may be.

It will be understood in the foregoing that the $R_1$ and $R_2$ groups in successive —P=N— repeating units/moieties of the phosphazene compounds may be the same as, or different from, one another. For example, the $R_1$ group in a first repeating unit or moiety of the phosphazene compound may be the same as or different from the $R_1$ group in the next and other repeating units/moieties in the phosphazene compound. Further, the $R_1$ and $R_2$ groups joined to each of the phosphorous atoms in the compound may differ independently from one another, or, alternatively, all of the individual $R_1$ and $R_2$ groups, each of which is independently selected relative to the other, may be the same on the respective phosphorous atoms.

The contrast agent according to the invention, comprising a halogenated, preferably iodinated or brominated, derivative of boron, e.g., an organic derivative of such type, advantageously possesses the following characteristics for its use in X-ray imaging:

a stability in water sufficiently high to enable it to withstand sterilization conditions, a high molar halogen concentration, especially iodine or bromine concentration, equal to at least 10%, preferably to at least 30% and, still more preferably, to at least 40%, and lower than 95%, a low osmolality, lower than 2000 mosmol/kg H$_2$O, preferably lower than 800 mosmol/kg H$_2$O, at useful concentrations, i.e., higher than 100 g of halogen, especially of iodine or of bromine, per liter, and a low toxicity corresponding to a LD$_{50}$ intravenously in mouse, higher than or equal to 2 g of halogen, especially of iodine or bromine per kg of body weight of the mouse.

Among the derivatives of the formula (I) discussed hereinabove, those of the following formula are preferred:

$$B_{12}H_{(12-y)}X_yM_x \qquad \text{(Ia)}$$

$$B_{12}H_{(2-y')}I_{10}X_yM_x \qquad \text{(Ib)}$$

$$B_{10}H_{(10-y)}X_yM_x \qquad \text{(Ic)}$$

and $$B_{10}H_{(2-y')}I_8X_yM_x \qquad \text{(Id)}$$

in which y, X, M and x are as indicated in connection with (I) and in which y' is an integer varying from 0 to 2.

Dimeric derivatives of $B_{12}$ and $B_{10}$ salts could also be employed (see Wiersema, R. J., et al, Inorg. Chem., Oct. 1969, pp. 2074–2079; and Chamberland, B. L., et al, Inorg. Chem., 3(10), Oct. 1964, pp. 1450–1456).

Particularly advantageous contrast agents according to the invention include those set out below:

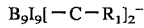

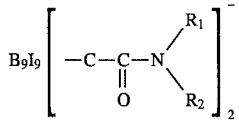

$B_{10}I_{10}^{2-}$
$B_{10}I_8Br_2^{2-}$
$B_{10}I_8H_2^{2-}$
$B_{10}I_8(NHCOCH_3)_2^{2-}$
$B_{10}I_8(CONH_2)_2^{2-}$
$B_{10}I_8(OCH_3)_2^{2-}$
$B_{10}I_8(CONHCH_2CHOHCH_2OH)_2^{2-}$
$B_{10}I_8[-NH-R_1]_2$

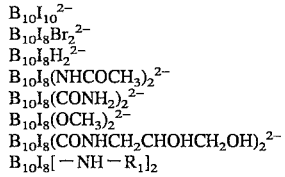

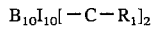

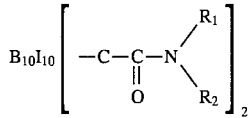

-continued

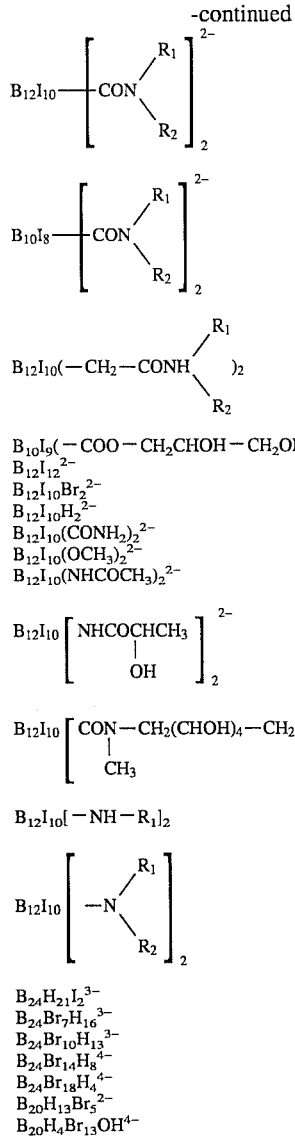

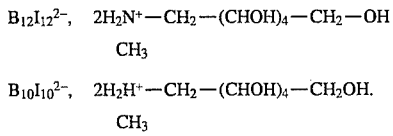

in which $R_1$ and $R_2$ are as defined above.

Physiologically acceptable salts of contrast agents according to the invention include the salts of meglumine (or Mgl), lysine (or Lys), arginine (or Arg), sodium, potassium, ammonium, calcium, and N-methyl-glucamine salts of the polyiodinated anions corresponding to the formulas $B_{12}I_{12}^{2-}$ and $B_{10}I_{10}^{2-}$, i.e.:

$$B_{12}I_{12}^{2-}, \quad 2H_2N^+-CH_2-(CHOH)_4-CH_2-OH$$
$$\qquad\qquad\qquad\qquad\qquad CH_3$$

$$B_{10}I_{10}^{2-}, \quad 2H_2H^+-CH_2-(CHOH)_4-CH_2OH.$$
$$\qquad\qquad\qquad\qquad\qquad CH_3$$

The present invention also comprehends the isomers of the derivatives of formula (I), especially the position isomers, the sterioisomers under optically active or racemic form.

A certain number of the above-mentioned compounds and especially the two polyiodinated anions above-identified are known as chemical products and disclosed in the publication "Inorg. Chem." 3, pages 159, 167 (1964); all these compounds can be prepared by use of the processes disclosed in such publication or in the publications identified hereinafter.

More particularly, the amides of formula

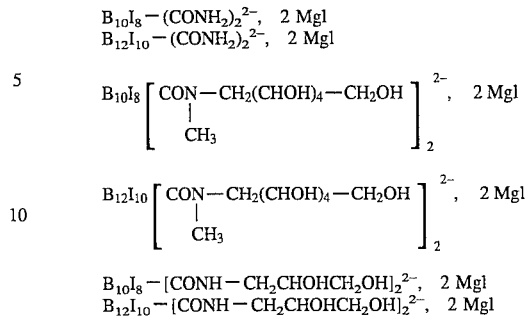

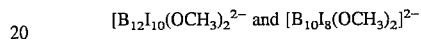

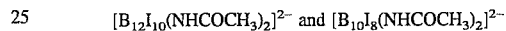

$$B_{10}I_8-[CONH-CH_2CHOHCH_2OH]_2^{2-}, \quad 2 \text{ Mgl}$$
$$B_{12}I_{10}-[CONH-CH_2CHOHCH_2OH]_2^{2-}, \quad 2 \text{ Mgl}$$

can be prepared by using the processes disclosed in JACS, Vol. 86, pages 115–116 (1964) and in JACS, Vol. 89, pages 4842–4850 (1967).

The alkoxy derivatives of formula (I):

$$[B_{12}I_{10}(OCH_3)_2]^{2-} \text{ and } [B_{10}I_8(OCH_3)_2]^{2-}$$

can be prepared by use of the processes disclosed in JACS, Vol. 86, pages 3973–3983 (1964).

The amide derivatives of formulas:

$$[B_{12}I_{10}(NHCOCH_3)_2]^{2-} \text{ and } [B_{10}I_8(NHCOCH_3)_2]^{2-}$$

can be prepared by use of the processes disclosed in JACS, 88, pages 935–939 (1966).

The halogenation techniques, especially iodination used for the preparation of the contrast agents according to the invention, are carried out in the presence of iodine and/or ICl, using the process disclosed in "Inorg. Chem.", Vol. 3, pages 159–167 (1964).

The preferred contrast agents according to the invention present particular features which are associated with their chemical structure and as a result of which they are especially adapted to X-ray imaging applications, especially a high stability and a concentration in radioopaque halogen atoms which is especially high when compared with the concentration in halogen atoms of the polyiodinated compounds conventionally used as contrast agents in the field of X-ray imaging.

The various compounds described hereinabove may be administered for X-ray imaging applications in any suitable non-salt forms as well as in the form of physiologically acceptable salts.

The contrast media agents of the present invention may be employed in any suitable formulation. A useful contrast medium formulation typically comprises the active ingredient (i.e., the radiopaque boron compound) together with one or more physiologically acceptable carriers thereof and optionally any other therapeutic or desired ingredients. The carrier(s) must be physiologically acceptable in the sense of being compatible with the other ingredients of the formulation and not unsuitably deleterious to the recipient thereof. The active agent ingredient is provided in an amount effective to achieve the desired radiopacity and radiological imaging effect, and in a quantity appropriate to such purpose.

An X-ray imaging composition according to the invention may therefore include at least one above-mentioned contrast agent in an aqueous solution or suspension, preferably in bidistillated water; the composition alternatively may be in the form of a powder.

By way of example, a radiological imaging contrast medium formulation of the present invention may comprise a sterile aqueous solution, for intravascular administration, as the diagnostic radiopaque medium employed in excretory urography, angiocardiography, or aortography, or in other contrast medium application.

The contrast medium formulation may usefully include adjuvants generally used in pharmaceutical compositions containing contrast agents, such as salts and buffers rendering the sterile aqueous solution isotonic with the receiving locus of the corporeal system to which the contrast medium formulation is administered. Useful adjuvant ingredients may include calcium disodium, monobasic sodium phosphate, sodium chloride, tris(hydroxymethyl)amino-methane hydrochloride, amine of (trishydroxymethyl)amino-methane, heparine, sodium citrate, and sodium calciedetate. Desirably, at least 15% by volume, based on the total volume of solution, of the formulation is chemically bound iodine deriving from boron compounds of the present invention, preferably at least 40%, and most preferably at least 50%, of iodine, on such volume basis.

In the case of an aqueous solution of the contrast agent of formula (I), the concentration desirably is from about 0.05M to about 1M, preferably from about 0.2M to about 0.5M per liter.

Thus, in addition to the boron compound(s), the contrast medium reagent formulation of the present invention may include salts, buffers, diluents, binders, disintegrants, surface active agents, thickeners, preservatives (including antioxidants), etc.

The administration of the boron compound-containing contrast medium formulation to the corporeal situs to be visualized, may be carried out in any suitable manner and with any efficacious means and methods. For example, the intravascular administration of contrast medium formulation may be effected by a catheter joined at one end to a vascular locus and in fluid introduction relationship therewith. The other end of the catheter may be joined to a suitable angiographic syringe, such as a Coeur 150 ml angiographic syringe, commercially available from Coeur Laboratories, Inc. (Raleigh, N.C., USA), as employed in a Medrad Mark V® angiographic injector, commercially available from Medrad, Inc. (Pittsburgh, Pa., USA).

The dosage of the contrast medium formulation, in the administration of the formulation to the corporeal situs, may be at any suitable level consistent with the imaging function to be carried out. By way of example, a formulation containing approximately 40% chemically bound iodine deriving from boron compound(s) therein, may be usefully employed for urographic, angiocardiographic, and/or aortographic applications, at an intravenous dosage in adults of 25–50 ml of the formulation, injected over a period of 15–120 seconds, and more preferably over a period of 30–90 seconds, so that peak blood values are obtained immediately following injection, and equilibration with extracellular compartments is attained in approximately 5–15 minutes.

In X-ray imaging applications, compositions containing X-ray contrast agents according to the invention, particularly those corresponding to formula (I) hereof, may be administered with a useful dose from about 10 to about 250 ml of aqueous solution containing from about 100 to about 500 g of halogen per liter, preferably from about 200 to about 400 g of halogen per liter.

Administration of the X-ray contrast agent formulation, provided it is in the form of aqueous solution, may be enterally or parenterally, especially orally, rectally, intravenously, intra-articularly, intra-arterially, sub-arachnoidly as well as bronchially, lymphatically and intra-uterinally.

In the case in which the X-ray contrast agent formulation is an aqueous suspension or a powder contained in a physiologically acceptable galenic formulation, the composition can be administered enterally, orally, rectally or bronchially.

In the case in which the X-ray contrast agent formulation according to the invention is in the form of a colloidal suspension, it suitably comprises the iodinated derivatives of boron in the form of insoluble particles of a size lower than 1 micron and preferably lower than 400 nm, suspended physiologically compatible solvent, preferably aqueous medium such as water, to carry out X-ray imaging of the vascular sector, of the liver, and of the lymphatic ganglions. As an example, an insoluble salt of $B_{10}I_{10}^{2-}$ may be provided in an aqueous suspension of 300 nm average diameter particles of the salt, at a salt concentration providing the requisite bioavailability in vivo.

Compositions according to the invention comprising the aforementioned contrast agents present especially advantageous osmolatities; for example, the dose of 35 g of iodine per 100 ml which is generally used in X-ray imaging is obtained, as long as a triiodinated compound of the prior art is used, with a solution whose concentration is about 0.9M, while it proves sufficient to use the solution based on a contrast agent according to formula (I) at a molar concentration from three to four times lower.

Set out below are a few examples of X-ray contrast agent formulations according to the invention in the form of aqueous solutions:

| | | |
|---|---|---|
| a) $B_{10}I_{10}^{2-}$ | 34.5 g | (0.25 M) |
| N-methylglucamine | 9.75 g | (0.5 M) |
| water for an injectable preparation | q.s.p. | 100 ml |
| b) $B_{10}I_{10}^{2-}$ | 34.5 g | (0.25 M) |
| NaOH | 1 g | (0.25 M) |
| N-methylglucamine | 4.88 g | (0.25 M) |
| water for an injectable preparation | q.s.p. | 100 ml |
| c) $B_{12}I_{10}(OCH_3)_2^{2-}$ | 36.5 g | (0.25 M) |
| N-methylglucamine | 9.75 g | (0.50 M) |
| water for an injectable preparation | q.s.p | 100 ml |
| d) $B_{12}I_{12}^{2-}$ | 33.08 g | (0.2 M) |
| N-methylglucamine | 7.8 g | (0.4 M) |
| water for an injectable preparation | q.s.p. | 100 ml. |

The pH of the above-mentioned solutions is suitably adjusted to a value between about 6.5 and about 7.5.

In certain particular uses, it may be advantageous, in connection with the diagnosis of a given pathology, especially at the level of a specific organ, to use what is called a "vectorization" of the contrast agent, which can be obtained for example by encapsulation of the agent within liposomes, or by its fixation or bonding on a macromolecule, polymer, microsphere (e.g., microbead), or other "anchoring" or "carrier" moiety.

The macromolecules adapted to be used in connection with such a use may be of biological or synthetic origin and especially selected among proteins, polyalkyamines, lipoproteins, glycoproteins, polysaccharides and polypeptides; for example, use can be made, as macromolecules of the kind in question, of starches, hydroxyethyl starches, arabinogalactans, dextrans, polylysins, albumin, poly and monoclonal antibodies, and star-shaped polymers called "dendrimers" (preferably polymers of such type having a weight average molecular weight in the range of from about 1000 to about 100,000 daltons).

Among the groups particularly adapted which are to be fixed on biological or synthetic macromolecules, those corresponding to the following formulas may be indicated:

$[B_{12}I_{10}X_2]^{2-}$ $[B_{10}I_8X_2]^{2-}$ $[B_9C_2I_9X_2]^-$ $[B_9C_2I_9HX]^-$ in which at least one of X is an activatable group (i) selected from the group consisting of $NH_2$, $CO_2H$, SH, OH, allyl (—CH=CH$_2$), and their derivatives and (ii) enabling the fixation on a macromolecule. This fixation is carried out by applying the methods which are classically used to carry out the coupling of non-iodinated boron derivatives on proteins or polysaccharides.

In that respect, the following publications are of interest:

"Journal of Immunological Methods", Vol. 126, 1990, pages 95–102,

"Appl. Radiat. Isot.", Vol. 38, 1987, pages 503–506,

"Proc. Int. Symp. Neutron Capture Ther. 1ST", 1983, pages 237–244.

As far as polysaccharides and especially dextrans and hydroxyethyl starch are concerned, the general activation methods can be used; in that respect, the publication "Advanced Drug Delivery", Reviews 3, 1989, pages 103–154 is of interest. Thus, activated dextran with $NaIO_4$ can react with an iodinated boron derivative comprising at least one group X equal to $NH_2$ in the presence of sodium cyanoborohydride.

The residual aldehydes are reduced using sodium borohydride and the resultingly obtained polymer is purified by way of dialysis.

The pathologies whose diagnosis can be facilitated by way of such a vectorization are especially tumoral pathologies, liver pathologies, and distribution abnormalities of the blood volume.

It will be recognized that the foregoing composition, dosage, and administration parameters are illustrative in character, and that the composition, dosage, and administration techniques may be varied widely in the broad practice of the present invention, within the skill of the relevant art.

Set out below is a description of the synthesis of borohydride compounds and salts, including halogenated derivatives comprising iodine reagent compounds potentially useful in the broad practice of the present invention.

It has been known since the early 1960's that salts of $B_{12}H_{12}^{2-}$ are thermally stable, and resistant toward degradation by acids, bases, and mild oxidizing agents, to a degree which is unique in boron hydride chemistry. The $B_{12}H_{12}^{2-}$ anion does react, however, with a variety of reagents to produce substitution derivatives, including halogen derivatives, which rival or exceed the thermal and chemical stability of $B_{12}H_{12}^{2-}$, and are potentially usefully employed in the practice of the present invention.

The icosahedral $B_{12}$ framework provides the basis for an entirely new generation of contrast media agents. The properties of the parent moiety, $B_{12}H_{12}^{2-}$ will be briefly described below, followed by a description of various halogenated (iodinated) species based on same.

Salts of $B_{12}H_{12}^{2-}$ a. Thermal Stability

By way of illustration, $Cs_2B_{12}H_{12}$ can be heated to 810° C. in an evacuated sealed quartz tube and recovered unchanged. It is also quite thermally stable in air.

b. Hydrolytic Stability $B_{12}H_{12}^{2-}$ salts show no reaction with strong aqueous sodium hydroxide even at 95° C. $B_{12}H_{12}^{2-}$ is stable to 3N HCl at 95° C.

c. Solubility

Extremely water soluble salts of $B_{12}H_{12}^{2-}$ are formed with cations such as ammonium, lithium, sodium, and alkaline earths.

d. Toxicity

The approximate lethal dose of $Na_2B_{12}H_{12}$, administered orally to rats, is greater than 7.5 gm/kg of body weight. This is approximately equal to the oral toxicity of sodium chloride. Massive doses of a closely related derivative, $Na_2B_{10}H_{10}$, have been given to humans without serious effect and the anion recovered from urine specimens. Such biological inertness is attributed to its chemical stability.

e. Structure

The twelve boron atoms in the $B_{12}H_{12}^{2-}$ anion have icosahedral symmetry, and each boron atom has an exopolyhedral hydrogen The volume of the $B_{12}H_{12}^{2-}$ ion is comparable to that swept out by a rotating benzene group.

f. Cost $B_{12}H_{12}^{2-}$ salts can be made in large quantities and at reasonable cost.

Halogenated Derivatives of $B_{12}H_{12}^{2-}$

Partially or completely chlorinated, brominated, and iodinated derivatives of $B_{12}H_{12}^{2-}$ have been prepared (see Knoth, W. H., et al, Inorg. Chem., 3, 159 (1964)).

Salts of $B_{12}H_{12}^{2-}$ a. Thermal Stability

The $B_{12}I_{12}^{2-}$ dianion, which contains about 93% iodine, suffers no degradation in 20% aqueous NaOH at 85° C., or $H_2SO_4$ at 150° C. Thus, its salts can be very easily sterilized. This remarkable stability suggests that this anion probably has very little toxicity, and also implies that there is essentially no dissociation to give free I—.

b. Hydrolytic Stability

Good hydrolytic stability characteristics are exhibited.

c. Solubility $Na_2B_{12}I_{12}$ has an unexpectedly high solubility in water.

d. Preparation

For the preparation of iodinated salts of $B_{12}H_{12}^{2-}$ (Knoth W. H., et al, ibid), the first two iodine atoms can be placed on the icosahedral cage by reaction of $I_2$ in accordance with the equation:

$$Na_2B_{12}H_{12} + 2I_2 \rightarrow Na_2B_{12}H_{10}I_2 + 2HI.$$

The reaction is complete in 10 minutes at room temperature. Solvents such as 1,1,2,2-tetrachloroethane or $CCl_4$ can be used. Even at this stage, the percent iodine in $B_{12}H_{10}I_2^{2-}$ is high (57.7%).

The remaining iodine atoms are added by reaction of $Na_2B_{12}H_{10}I_2$ with ICl:

$$Na_2B_{12}H_{12}I_2 + 10ICl \rightarrow Na_2B_{12}I_{12} + 10HCl.$$

Table I below presents molecular weight data on some $B_{12}H_{12}^{2-}$ salts and iodinated derivatives and the % iodine in the latter.

TABLE I

Molecular Weight of $B_{12}H_{12}^{2-}$ Salts,
Iodinated $B_{12}$ Salts and % Iodine

| Hydride Salts | M.Wt. | Iodinated Salts | M.Wt. | % I |
|---|---|---|---|---|
| $Li_2B_{12}H_{12}$ | 155.6 | $Li_2B_{12}I_{12}$ | 1654 | 92.1 |
| $Na_2B_{12}H_{12}$ | 187.7 | $Na_2B_{12}I_{12}$ | 1700 | 89.6 |
| | | $MgB_{12}I_{12}$ | 1678 | 90.8 |
| $Cs_2B_{12}H_{12}$ | 407.5 | $Cs_2B_{12}I_{12}$ | 1919 | 79.4 |
| | | $Na_2B_{12}F_4I_8$ | 1268 | 80.1 |
| | | $Na_2B_{12}H_4I_8$ | 1196 | 84.5 |
| | | $Na_2B_{12}H_{10}I_2$ | 440 | 57.7 | e. Viscosity

X-ray contrast agent formulations already known in the art are characterized by high viscosity, typically between 5 to 20 mpasc.s at 37° C. and at 32 g iodine/100 cm³ of solution.

f. Osmolality Considerations

X-ray contrast agents based upon polyiodinated benzene derivatives are customarily formulated such that 100 cm³ of sterile solution containing 32 grams of iodine (60 grams of whole product) are injected. This represents a water solubility of about 1M.

For $Na_2B_{12}I_{12}$ (89.6%.I) to obtain 32 gm I in 100 cm³ of solution, only 35.7 gm of $Na_2B_{12}I_{12}$ are needed. The resulting solution is 0.21M in $Na_2B_{12}I_{12}$.

Since osmolality is proportional to the number of dissolved particles, a 0.21M solution of $Na_2B_{12}I_{12}$ would (ideally) behave as a 0.63M solution of a non-ionic contrast agent. Thus, even though $Na_2B_{12}I_{12}$ is an ionic compound, because of its exceptionally high iodine percent, the osmolality of solutions containing the required amount of iodine (32 gm I/100 cm³) would (ideally) still be less than non-ionic organic iodinated solutions of approximate 1M. For example, a solution of $B_{12}I_{12}^{2-}$ $2Na^+$ of 0.24M is characterized by an osmolality of 680 mosmol.kg.

Solutions of $B_{12}I_{12}^{2-}$ of lower osmolality than those of the sodium salts can be made, e.g., utilizing $MgB_{12}I_{12}$. Passage of $Na_2B_{12}I_{12}$ through an acid ion exchange column may be employed to produce the conjugate acid, $(H_3O^+)_2B_{12}I_{12} \cdot xH_2O$, followed by reaction with MgO or $MgCO_3$ to give $MgB_{12}I_{12}$:

$$MgCO_3 + (H_3O^+)_2B_{12}I_{12} \rightarrow MgB_{12}I_{12} + 2H_2O + CO_2$$

A 0.21M solution of $MgB_{12}I_{12}$ (90.8% I) contains 32 gm I/100 cm³, and behaves (osmolality-wise) as a 0.42M solution of a non-ionic compound.

By way of comparison, a 0.42M solution of Iotrol (molecular weight 1,626 and 46.8% I), 32 gm I/100 cm³, has an osmolality of 300; thus, a 0.21M solution of $MgB_{12}I_{12}$ (0.42M in particles) has an ideal osmolality comparable to Iotrol.

g. Synthesis $Li_2B_{12}H_{12}$ and $Na_2B_{12}H_{12}$ can be made in almost quantitative yield from $LiBH_4$ or $NaBH_4$. The theoretical yield of $Na_2B_{12}I_{12}$ from 1 kg of $Na_2B_{12}H_{12}$ is 1×1700/187.7=9.05 kg.

The laboratory preparation of $Na_2B_{12}I_{12}$ involves only the addition of 12 followed by ICl (to a solution of $Na_2B_{12}H_{12}$), or essentially a one-step reaction.

h. Viscosity Considerations 32 grams of I per 100 cm³ of solution is easily obtained by solutions of $B_{12}I_{12}^{2-}$ around 0.2M; viscosity is unexpectedly low.

i. Water Stability

Salts of $B_{12}I_{12}^{2-}$ are readily sterilizable. $B_{12}I_{12}^{2-}$ suffers no degradation in $H_2SO_4$ at 150° C., or in 20% aqueous NaOH at 85° C.

Derivative Formation

There is an extensive literature on the derivatization of $B_{12}H_{12}^{2-}$ (and $B_{10}H_{10}^{2-}$) which is concisely described in "The Chemistry of Boron and its Compounds", Earl L. Muetterties, Ed., Chapter 6, Boron Hydrides, by M. F. Hawthorne, John Wiley & Sons, Inc., New York (1967), the disclosure of which hereby is incorporated herein by reference.

One general approach to derivative synthesis is direct substitution on $B_{12}H_{12}^{2-}$, followed by modification of the species thus formed (including halogenation). One attractive feature of the derivative chemistry of $B_{12}H_{12}^{2-}$ is that substitution can bring about a change in net charge, yielding the possibility of preparing (iodinated) polyhedral boron compounds of varying charge. Thus, anions, e.g., of net −1 charge, neutral species, non-ionic species, and even cations are feasible.

An exemplary list of substituted $B_{12}H_{12}^{2-}$ species and their analogs (iodinated derivatives) is set out in Table II below.

TABLE II

Substituted $B_{12}H_{12}^{2-}$ Species and Related
Iodinated (or Brominated) Derivatives

| Substituted $B_{12}H_{12}^{2-}$ | Iodinated (or Brominated) Derivatives |
|---|---|
| $B_{12}H_{11}OH^{2-}$ | $B_{12}I_{11}OH^{2-}$ |
| $B_{12}H_{10}(OH)_2^{2-}$ | $B_{12}I_{10}(OH)_2^{2-}$ |
| $B_{12}H_{10}(COOH)_2^{2-}$ | $B_{12}I_{10}(COOH)_2^{2-}$ |
| $B_{12}H_{10}(CO)_2$ | $B_{12}I_{10}(CO)_2$ |
| $B_{10}H_8(CO)_2$ | $B_{12}I_8(CO)_2$ |
| $B_{12}H_{10}(N_2)_2$ | $B_{12}I_{10}(N_2)_2$ |
| $B_{12}H_{10}[N(CH_3)_2CH_2Cl]^{2-}$ | $B_{12}I_{10}[N(CH_3)_2CH_2Cl]^{2-}$ |
| $B_{12}H_{10}(NH_3)_2$ | $B_{12}I_{10}(NH_3)_2$ |

The examples shown in Table II above are illustrative of a wide variety of potential halogen-substituted polyhedral boron species. Most have outstanding hydrolytic and oxidative stability, and high halogen content.

An exemplary contrast media reagent formulation may for example comprise $B_{12}I_{10}(NH_3)_2$. This non-ionic derivative contains close to 89% I and is water-soluble. There are a number of routes to its preparation. Other preferred reagent species from the foregoing listing include $B_{12}I_{10}(CH_2NH_3)_2$ and $B_{12}I_{10}(CH_2OH)_2^{2-}$.

Molecular dimers of the halogenated polyhedral boron compounds may be synthesized to produce radiopaque particles which are larger than normal capillaries fenestration. This limits distribution of the boron compounds to the intravascular space in the use of contrast media formulations containing such boron compounds.

Cyclophosphazene- and Polyphosphazene-Based
Contrast Media Agents

Cyclophosphazenes and polyphosphazenes constitute a class of compounds which may be employed as "backbone" or "framework" chemical structures to which active moieties of currently used contrast media agents, as well as active moieties of the above-discussed boron species, may be attached.

Cyclophosphazenes, such as $(Cl_2PN)_3$, are based on alternating P and N atoms:

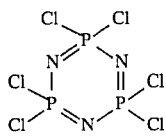

More specifically, cyclophosphazenes usefully employed in the broad practice of the present invention have the following formula:

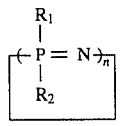

wherein:

$R_1$ and $R_2$ may be the same or different, and are independently selected from hydrogen, halo, and organo groups (e.g., alkyl, haloalkyl, aryl, arylalkyl, alkenyl, alkylamino, arylamino, etc.); and n is from 3 to 8;

with the proviso that at least one of the $R_1$ and $R_2$ groups comprises at least one iodine atom and at least one boron atom, and that 6he compound is of a radiopaque character. Polyphosphazenes comprise a P—N chain backbone and have the following formula:

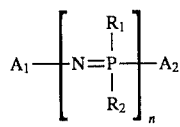

wherein:

$A_1$, and $A_2$ are end groups which may be of any suitable organic constituency which is compatible with the polyphosphazene and does not preclude its efficacy for radiological imaging purposes—$A_1$ and $A_2$ may be the same or different, and may for example comprise alkyl or other hydrocarbyl radicals;

$R_1$ and $R_2$ may be the same or different, and are independently selected from hydrogen, halo, and organo groups (e.g., alkyl, haloalkyl, aryl, arylalkyl, alkenyl, alkylamino, arylamino, etc.); and n is from 2 to 20,000;

with the proviso that at least one of the $R_1$ and $R_2$ groups comprises at least one iodine atom and at least one boron atom; and which is of a suitable radiopaque character.

The compound $(Cl_2PN)_3$ is a white, crystalline material prepared from phosphorous pentachloride and ammonium chloride. The P—Cl bonds are highly reactive, reacting readily with nucleophiles such as alkoxides, aryloxides, amines, etc., to give completely substituted derivatives.

The $(Cl_2PN)_3$ compound may be usefully employed to construct "non-ionic" contrast media agents. For example, a triiodo benzene species could be used to partially derivatize the $(Cl_2PN)_3$ ring, followed by derivatization with appropriate groups to confer aqueous solubility:

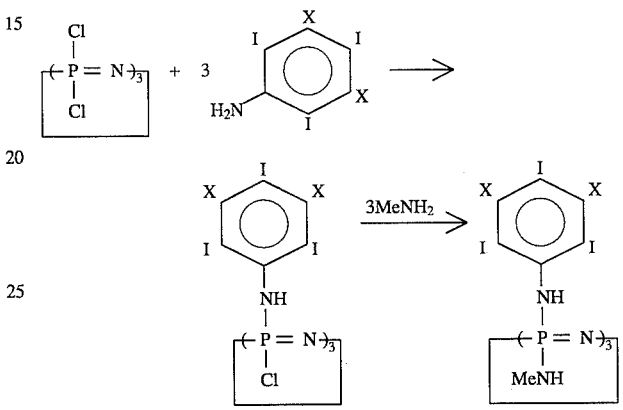

wherein X=H and $H_2O$ solubility is conferred by the MeNH groups on the phosphorous atoms of the compound.

Instead of the above-described halogenated benzenes, halogenated boron compounds may be usefully employed to synthesize boron-based contrast media reagents according to the present invention. Thus, species such as shown below can be constructed which possess high water solubility and high I content:

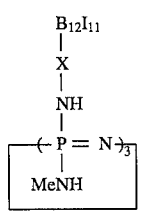

wherein X is an appropriate linking or bridge moiety, e.g., an amino or alkoxide linker moiety.

Synthesis of polyphosphazenes may be effected as shown below:

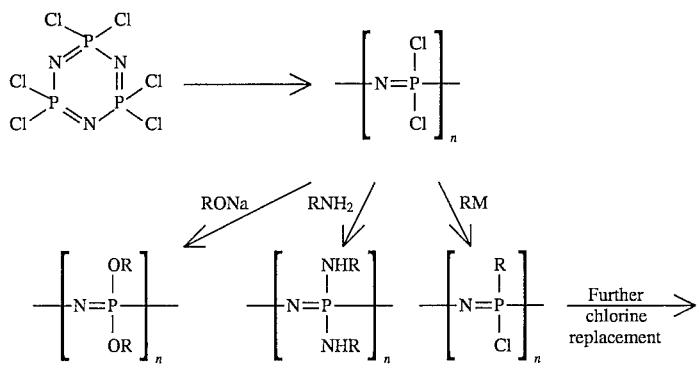

The reactive chloride atoms of the starting material in these reactions can be replaced with nucleophiles such as amines, alkoxides, aryloxides, etc.

Of particular interest in the manufacture of contrast media reagents according to the present invention is the synthesis approach of partial substitution of $Cl^-$ with triiodinated phenoxide or iodinated $B_{12}$ species. The remaining chlorides then can be replaced with substituents to confer water solubility, such as $MeNH-$, glycerol, etc.

The water-soluble polyphosphazene polymers described above desirably contain hydrolyzable groups capable of producing a degradable polymer. For example, an amino acid such as glycine can be attached via a P—N bond. Hydrolysis of the P—N bonded amino acids gives a P—OH bond. The hydrophosphazenes are hydrolytically unstable, decomposing to harmless phosphate and ammonia, thereby permitting a highly iodinated polymeric contrast media reagent to be synthesized with the capability to eventually erode and be excreted from the body.

The features and advantages of the present invention are further illustrated by the following examples.

EXAMPLE X 35.7 grams of $Na_2B_{12}I_{12}$ are added to a sterile aqueous solution buffered with a monobasic sodium phosphate buffer, to provide 100 cc of solution. Aqueous solution of $B_{12}I_{12}^{2-}$, $2Na^+$ at 0.24M is characterized by an unexpected low viscosity at this iodine concentration of 1.5 mpasc.s at 37° C. and low osmolality of 680 mosmol.kg water and high stability with no release of iodide after sterilization. 50 milliliters of the solution are intravenously administered over a period of approximately 60 seconds, using a Coeur® 150 ml angiographic syringe (Coeur Laboratories, Inc., Raleigh, N.C., USA) connected by a luer-lock coupling to a catheter which is joined at its opposite end by venous shunt to the vascular administration site. The administration is effected by a Mark V® angiographic power injector (Medrad Corporation, Pittsburgh, Pa., USA), with the syringe being appropriately positioned in the injector jacket of the automatic injector apparatus. Peak blood values are attained immediately following injection. The blood concentration falls rapidly over the next 5–10 minutes, and equilibration with the extracellular compartments is attained in approximately 10 minutes. The vascular situs is visualized by impingement of an X-ray beam on such situs, from an X-ray generator comprising an X-ray tube with a collimator serving as a beam-limiting device. The X-ray beam has a photon energy of above 20 keV.

A radiographic image is produced of the vascular situs, and is employed to determine whether occlusion of the vascular lumen has occurred and whether angioplasty is an appropriate therapeutic intervention.

The contrast media formulation is excreted rapidly unchanged by renal glomerular filtration.

EXAMPLE Y

The procedure of Example X is repeated using a contrast media formulation comprising $B_{12}I_{10}(NH_3)_2$, and the efficacy of such reagent compound is demonstrated.

EXAMPLE Z

The procedure of Example X is repeated with various cyclophosphazenes and polyphosphazenes, comprising at least 40% iodine deriving from boroiodide pendent functionality which is bonded directly or indirectly (via an amino or alkoxide divalent linker group) to a phosphorous atom of the reagent, and the efficacy of such reagent compounds is demonstrated.

The present invention preferably is carried out with a halogenated derivative of boron having (i) a stability in water sufficiently high to enable it to withstand sterilization conditions, (ii) a molar halogen concentration of at least 40% and lower than 95%, (iii) an osmolality lower than 800 mosmol/kg $H_2O$ at concentrations higher than 100 g of halogen, and (iv) a low $LD_{50}$ mouse toxicity at least equal to 2 g of halogen per kg of body weight of the mouse.

A highly preferred class of contrast agents is the class of derivatives of boron of the formula (I) set out hereinabove, including the salts of such derivatives of formula (I), such as salts of meglumine, lysine, arginine, sodium, calcium, N-methyl-glucamine, as hereinabove described.

The contrast agent formulations suitably comprise aqueous solutions wherein, when the contrast agent is of formula (I), the concentration of contrast agent is from about 0.2M to about 0.5M per liter, wherein the solvent medium of the contrast agent formulation preferably is bidistilled water, and wherein the formulation contains conventional-type pharmaceutical composition adjuvants, such as sodium chloride, tris(hydroxymethyl)amine-methane hydrochloride, amine of tris(hydroxymethyl) amine-methane, heparine, sodium citrate and sodium calciedetate.

In use for X-ray imaging, such aqueous solutions are preferably administered in doses ranging from about 10 to about 250 ml of aqueous solution containing from about 200 to about 400 g of halogen per liter. Administration may be enterally or parenterally and preferably is oral, rectal, intravenous, intra-articular, intra-arterial, sub-arachnoidal, bronchial, lymphatical, or intra-uterine.

In another preferred form for administration, the X-ray contrast agent of the invention may be in sub-micron powder form comprising particles preferably less than 400 nm in average particle diameter, suspended in a physiologically compatible solvent as a colloidal suspension.

Presently preferred X-ray contrast agent formulations according to the present invention include the N-methylglucamine formulations (a)–(d) set hereinabove, having a pH of from about 6.5 to about 7.5.

In vectorized form, the X-ray contrast agents preferably are encapsulated within liposomes or associated with biomolecules such as proteins, lipoproteins, glycoproteins, polysaccharides, polypeptides, dextrans, polylysins, albumin, monoclonal and polyclonal antibodies, and dendrimers.

In application the X-ray imaging contrast agents of the invention are usefully employed in biocompatible imaging compositions for the radiological imaging and visualization of corporeal sites, for purpose of diagnosis and treatment of physiological conditions. The imaging compositions are radiopaque in character and thus when administered to a body mart or other corporeal site, permit the appertaining body region to be subjected to radiation (X-rays) and fluoroscopic analysis. Radiological imaging applications within the broad scope of the invention include excretory urography, angiocardiography, and aortography. Specific examples include coronary angioplasty determination, wherein the contrast agent formulation is introduced into a coronary lumen, and gynocological imaging wherein the contrast agent formulation is transcervically introduced for radiological visualization of the pelvic region.

Accordingly, the X-ray contrast agents, compositions, and methods of the present invention have broad utility in the visualization, diagnosis, and treatment of animal, e.g., mammalian, subjects, particularly humans.

What is claimed is:

1. A method of imaging a corporeal situs using x-ray imaging means, comprising delivering to the corporeal situs an imagingly effective amount of a physiologically acceptable contrast medium formulation containing a radiopacity-imparting boron compound, and thereafter visualizing the corporeal situs with said x-ray imaging means, wherein the boron compound comprises a compound selected from the group consisting of iodinated boron salts of the formula:

$$M_xB_nH_{n-y}I_y$$

wherein:

M is a monovalent or divalent cation;

x is 1 when M is divalent and 2 when M is monovalent;

n is 3 to 14; and y is 1 to 14, and derivatives thereof.

2. A method according to claim 1, wherein the boron compound comprises a compound selected from the group consisting of iodinated boron salts of the formula:

$$M_xB_nH_{n-y}I_y$$

wherein:

M is an alkali metal or alkaline earth metal;

x is 1 when M is divalent and 2 when M is monovalent;

n is 10 to 12; and y is 2 to 12, and derivatives thereof.

3. A method according to claim 1, wherein M is selected from the group consisting of lithium, sodium, magnesium, and cesium.

* * * * *

UNITED STATES PATENT AND TRADEMARK OFFICE
CERTIFICATE OF CORRECTION

PATENT NO. : 5,545,397
DATED : August 13, 1996
INVENTOR(S) : Bernard F. Spielvogel and Dominique Meyer Page 1 of 2

It is certified that error appears in the above-indentified patent and that said Letters Patent is hereby corrected as shown below:

Column 3, Line 18  "per so" should read -- per se --

Column 3, Line 43  "$(B_nC_mH_{(m+n-y)})M_x$" should read -- $(B_nC_mH_{(m+n-y)}X_y)M_x$ --

Column 8, Line 32  after "with" insert -- formula --

Column 9, Line 55  "$2H_2H^+$" should read -- $2H_2N^+$ --

Column 10, Line 1  after "formula" insert -- (I): --

Column 10, Line 45  after "forms" insert -- , --

Column 12, Line 8  after "suspended" insert -- in --

Column 14, Line 18  after "hydrogen" insert -- bond. --

Column 15, Line 61  "12" should read -- $I_2$ --

Column 17, Line 29  "6he" should read -- the --

Column 18, Line 45  "NH" should be deleted

UNITED STATES PATENT AND TRADEMARK OFFICE
CERTIFICATE OF CORRECTION

PATENT NO. : 5,545,397
DATED : August 13, 1996
INVENTOR(S) : Bernard F. Spielvogel and Dominique Meyer It is certified that error appears in the above-indentified patent and that said Letters Patent is hereby corrected as shown below:

Column 21, line 22 "mart" should read --part--.

Signed and Sealed this

Twenty-fifth Day of November, 1997

Attest:

BRUCE LEHMAN

Attesting Officer

Commissioner of Patents and Trademarks